(12) United States Patent
Ganzi

(10) Patent No.: US 6,568,282 B1
(45) Date of Patent: May 27, 2003

(54) METHOD AND APPARATUS FOR EVALUATING A MEMBRANE

(75) Inventor: Gary C. Ganzi, Lexington, MA (US)

(73) Assignee: United States Filter Corporation, Palm Desert, CA (US)

( * ) Notice: Subject to any disclaimer, the term of this patent is extended or adjusted under 35 U.S.C. 154(b) by 0 days.

(21) Appl. No.: 09/513,414

(22) Filed: Feb. 25, 2000

Related U.S. Application Data
(60) Provisional application No. 60/121,798, filed on Feb. 26, 1999.

(51) Int. Cl.$^7$ .............................................. G01F 1/34
(52) U.S. Cl. ....................................... 73/861.42; 73/38
(58) Field of Search ............................. 73/38, 861.42; 210/87, 90

(56) References Cited

U.S. PATENT DOCUMENTS

| | | |
|---|---|---|
| 3,336,793 A | 8/1967 | Tuttle |
| 4,200,690 A | 4/1980 | Root et al. |
| 4,304,122 A * | 12/1981 | Tentor ........................... 73/38 |

(List continued on next page.)

FOREIGN PATENT DOCUMENTS

| | | | |
|---|---|---|---|
| EP | 0 314 822 * | 5/1989 | .......... G01F/11/28 |
| EP | 0 582 822 B1 | 2/1994 | |
| EP | 0 582 822 A1 | 2/1994 | |
| EP | 0 592 066 | 4/1994 | |
| EP | 0 640 822 A3 | 1/1995 | |
| EP | 0 638 798 B1 | 2/1995 | |
| EP | 0 638 798 A1 | 2/1995 | |
| EP | 0 640 822 A2 | 3/1995 | |
| EP | 0 640 822 B1 | 3/1995 | |
| EP | 0 831 318 A1 | 3/1998 | |
| FR | 2 749 190 | 12/1997 | |
| WO | WO 94/09890 A1 | 5/1994 | |
| WO | WO 94/09890 | 11/1994 | |
| WO | WO 96/28236 | 9/1996 | |

OTHER PUBLICATIONS

Bates, Wayne T., "Reducing the Fouling Rate of Surface and Waste Water RO Systems," Hydranautics, IWC–98–08, pp 1–7.

Blosse, Philip T. et al., "Diminutive bacteria: Implications for sterile filtration," American Biotech Laboratory, vol. 16, #12, pp 38–40.

Leahy, Timothy J. et al., "Validation of bacterial–retention capabilities of membrane filters," Pharmaceutical Technology, Nov., 1978, pp 65–75.

McFeters, Gordon A. et al., "Comparative performance of Colisure," Journal AWWA, vol. 89, Issue 9, pp 112–120.

Muilenberg, Thomas, "Microfiltration Basics: Theory and Practice," General Filter Company, pp 695–702.

(List continued on next page.)

*Primary Examiner*—Daniel S. Larkin
*Assistant Examiner*—Charles D. Garber
(74) *Attorney, Agent, or Firm*—Wolf, Greenfield & Sacks, P.C.

(57) ABSTRACT

A method and apparatus for evaluating a porous membrane. The method includes supplying a fluid to a first side of a wetted membrane at a pressure that is greater than the pressure on a second side of the membrane which is at a pressure greater than atmospheric pressure. The rate of transfer of the fluid from the first side to the second side is measured. The invention also includes an apparatus that includes a membrane mounted in a housing that divides the housing into a first compartment and a second compartment. A first fluid is contained in the first compartment at a pressure greater than the pressure in the second compartment. A second fluid is contained in the second compartment at a pressure greater than atmospheric pressure, and a measuring device is in communication with the first compartment, the second compartment, or both compartments.

25 Claims, 1 Drawing Sheet

U.S. PATENT DOCUMENTS

| | | | |
|---|---|---|---|
| 4,384,474 A | 5/1983 | Kowalski | |
| 4,385,517 A | 5/1983 | Sorce et al. | |
| 4,449,392 A | 5/1984 | Huschke | |
| 4,515,007 A | 5/1985 | Herman | |
| 4,614,109 A | 9/1986 | Hofmann | |
| 4,744,240 A | 5/1988 | Reichelt | |
| 4,812,407 A | 3/1989 | Buchmann et al. | |
| 4,872,974 A | 10/1989 | Hirayama et al. | |
| 4,881,176 A | 11/1989 | Kononov | |
| 4,909,937 A | 3/1990 | Hoffmann et al. | |
| 5,245,859 A * | 9/1993 | Smith et al. | 73/38 |
| 5,282,380 A | 2/1994 | DiLeo et al. | |
| 5,353,630 A | 10/1994 | Soda et al. | |
| 5,417,101 A | 5/1995 | Weich | |
| 5,468,388 A | 11/1995 | Goddard et al. | |
| 5,477,155 A | 12/1995 | Proulx et al. | |
| 5,480,554 A | 1/1996 | Degen et al. | |
| 5,563,344 A | 10/1996 | Kaiser et al. | |
| 5,576,480 A | 11/1996 | Hopkins et al. | |
| 5,581,017 A | 12/1996 | Bejtlich, III | |
| 5,594,161 A | 1/1997 | Randhahn et al. | |
| 5,616,828 A * | 4/1997 | Kucxenski | 73/38 |
| 5,674,404 A | 10/1997 | Kenley et al. | |
| 5,685,991 A | 11/1997 | Degen et al. | |
| 5,786,528 A * | 7/1998 | Dileo et al. | 73/38 |
| 5,918,264 A | 6/1999 | Drummond et al. | |
| 6,202,475 B1 * | 3/2001 | Selbie et al. | 73/38 |
| 6,324,898 B1 * | 12/2001 | Cote et al. | 73/38 |

OTHER PUBLICATIONS

Soules, W. J., "Filtration/Separation Techniques: Filter Cartridge Standards," Chemical Engineering Progress, vol. 70, No. 12, pp 43–45.

Chellam et al., "Modeling and Experimental Verification of Pilot–Scale Hollow Fiber, Direct Flow Microfiltration with Periodic Backwashing", Environ. Sci. Technol., 1998, vol. 32, pp. 75–81.

W. Doyen, "Latest Developments In Ultrafiltration For Large–Scale Drinking Water Applications", Desalination, 1997, vol. 113, pp. 165–177.

Gagliardo et al., "Membranes As An Alternative To Disinfection", Proc. Annv. Conf., Am. Water, 1997, pp. 427–445.

Glucina et al., "Assessment Of A Particle Counting Method For Hollow Fiber Membrane Integrity", Desalination, 1997, vol. 113, pp. 183–187.

John Gregory, "Turbidity and Beyond", Filtration and Separation, Jan./Feb. 1998.

Peter Hillis, "Full–Scale Application of Membrane Microfiltration In North West Water Huntington Stage 4, Provision of an 80 Mld Plant", Desalination, 1997, vol. 113, pp. 267–272.

Jacangelo et al., "Role of Membrane Technology In Drinking Water Treatment in the United States", Desalination, 1997, vol. 113, pp. 119–127.

Johnson, "Predicting Log Removal Performance of Membrane Systems Using In–Situ Integrity Testing", Filtration and Separation, Jan./Feb. 1998, pp. 26–29.

Johnston et al., "Certain Imprecisions in the Bubble Point Measurement", Jour. of Parenteral Science and Technology, 1981, vol. 35, pp. 36–39.

Warren T. Johnson, "Automatic Monitoring of Membrane Integrity In Microfiltration Systems", Desalination, 1997 vol. 113, pp. 303–307.

Kirby et al., "The Development of a Fine Particle Monitor Based on the Method of Dynamic Light Extinction", Filtration and Separation, Jan./Feb. 1998, pp. 73–77.

Logsdon et al., "Crptosporidium and Giardia Contamination and Removal", Proc. EPA Nat'l Drinking Water, 1996, pp. 1–23.

Meltzer, T. H., "High Purity Water Preparation For the Semiconductor, Pharmaceutical, and Power Industries", Chapter 5 Tall Oak Publishing, Littleton, CO 1993, pp. 219–240.

Nederlof et al., "Integrity of Membrane Elements, Vessels and Systems", Desalination, 1997, vol. 113, pp. 179–181.

W.P. Olson, "A System for Integrity Testing of Disc and Cartridge Membrane Filters", Pharmaceutical Technology, May 1982, pp. 42–52.

W.P. Olson et al., "Diffusion and Bubble Point Testing of Microporous Cartridge Filters: Preliminary Results at Production Facilities", J. Par. Sci. and Tech., 1981, vol. 35, pp. 215–222.

Ongerth et al., "DE Filtration To Remove Cryptosporidium", Journal AWWA, 1997, vol. 89, pp.39–46.

G. Reichelt, "Bubble Point Measurements On Large Areas of Microporous Membranes", J. Memb. Sci., 1991, vol. 60, pp. 253–259.

H.G. Schroeder et al., "Theoretical Aspects of Sterile Filtration and Integrity Testing", Pharmaceutical Technology, 1980, pp. 80–85.

Roessler, "Control of Cryptosporidium In Bottled Water using Cartridge Filtration Systems", Filtration and Separation, Jan./Feb. 1998, pp. 37–39.

Robinson et al., "Research Needs For Small Water Systems: A Survey", J. AWWA, Jan. 1997, vol. 89, pp. 101–113.

"Standard Test Method for Pore Size Characteristics of Membrane Filters Using Automated Liquid Porosimeter", ASTM E 1294–89, pp. 1–2.

"Standard Test Method for Pore Size Characteristics of Membrance Filters by Bubble Point and Mean Flow Pore Test", ASTM, F 316–86, pp. 752–757.

"Standard Test Method for Liquid Flow Rate of Membrance Filters", ASTM, F 317–72, pp. 764–765.

"Millex®/Sterives™ Integrity Tester", Millipore Owner's Manual.

"Integritest™ Exacta Integrity Tester" Millipore Owner's Manual.

"Validation Guide for Pall Microza Polysulfone 6,000 MWCO Ultrafiltration Modules", Pall Corp., 1994.

"Pall Unltrafine Filtration Company Brochure", P109310M, 1993.

"Communication from Pall Company concerning endotoxin removal," 1997.

"VIP Operating Instructions," Pall Company, 1995.

"SP Operating Instructions," Pall Company, 1994.

"General Water with LGV Presentation," Pall Company, 1997.

International Search Report PCT/US 00/04886, dated Jun. 29, 2000.

Hofmann, Frieder, "Integrity Testing of Microfiltration Membranes," Journal of Parenteral Science and Technology, vol. 38, No. 4, Jul.–Aug. 1984, pp. 148–159.

* cited by examiner

METHOD AND APPARATUS FOR EVALUATING A MEMBRANE

RELATED APPLICATIONS

This application claims priority to U.S. provisional application Ser. No. 60/121,798, filed Feb. 26, 1999, entitled "Removal of Particles from a Liquid," the disclosure of which application is incorporated herein by reference.

BACKGROUND OF THE INVENTION

1. Field of the Invention

The invention provides for a method and apparatus for evaluating a membrane and, in particular, a method and apparatus for evaluating the integrity of porous membranes used in water treatment systems.

2. Description of the Related Art

Various methods are available for testing the integrity of a porous membrane. These methods include, for example, a traditional challenge test, where a sample of water containing microorganisms is passed through the membrane and the downstream product is analyzed for the presence and concentration of the microorganism. Other methods do not generally use actual microorganisms but measure some other physical characteristic of the membrane that in some way reflects the membrane's ability to exclude the particles, solutes, or microorganisms of concern. These tests include the diffusion test, the bubble point test, the pressure hold test, turbidity measurements, particle counting, and conductivity tests.

In a standard diffusion test (DT), the membrane being tested is wetted with one fluid which is immiscible with a second fluid that is in contact with one side of the membrane. The pressure of the second fluid, typically air, is increased to a predetermined pressure or flow rate, generally one that has been recommended by the manufacturer of the membrane. At this pressure or flow rate, an amount of the second fluid will diffuse through the wetted membrane to the side of lower pressure. If the measured rate is the same as the rate suggested by the manufacturer, the membrane may be considered to be performing properly.

In the bubble point test (BPT), which is run in a similar manner to the diffusion test but at an increasing rate of pressure or flow of the second fluid, when the pressure of the second fluid reaches a critical level, the second fluid, typically air, may have expelled some of the wetting fluid from the pores of the membrane and may be visible as a series of bubbles on the low pressure side of the membrane. The lower the pressure required to produce visible bubbles, the greater the pore size or the size of a defect that may be present in the membrane. In addition to visually detecting the bubble point, the formation of bubbles may also be detected through the use of acoustic or optical measurements.

Measuring turbidity and counting particles have also been used to evaluate membranes. Both of these techniques provide general measurements of the amount of undissolved material that is passing through a membrane.

Another technique for measuring the amount of intrusion of a second fluid into a membrane is to measure the conductivity across a membrane. In this test, when a generally non-conductive membrane is intruded by a conductive fluid, the conductivity across the membrane increases and can be measured. From this measurement, the amount of fluid intrusion into the membrane can be indirectly determined.

SUMMARY OF THE INVENTION

The present invention is directed to a method and apparatus for evaluating a membrane. In one embodiment of the invention a fluid is supplied to the first side of a membrane at a pressure that is greater than the pressure on the second side of the membrane. The pressure on the second side of the membrane is an effective pressure greater than atmospheric pressure. The rate of transfer of the fluid from the first side of the membrane to the second side of the membrane is measured.

In another embodiment of the invention, a method for testing the integrity of a membrane is provided. A first side of a membrane is pressurized to a pressure greater than the pressure on the second side of the membrane and the pressure on the second side of the membrane is an effective pressure greater than atmospheric pressure. The amount of fluid transferred from the first side of the membrane to the second side of the membrane is measured and this amount is compared to the amount of fluid that would be predicted to be transferred by calculating the expected flow through a defect of a specific size.

In another embodiment, the present invention provides for a membrane testing apparatus. The apparatus includes a housing and a membrane mounted therein. The housing is divided into a first compartment and a second compartment. A fluid is contained in the first compartment at a pressure that is greater than the pressure in the second compartment and the pressure in the second compartment is an effective pressure greater than atmospheric pressure. A flow meter is in communication with the fluid.

In another embodiment, the invention provides for a membrane evaluation system that includes a wetted porous membrane having a first side and a second side. The pressure on the first side is greater than the pressure on the second side and the pressure on the second side is an effective pressure greater than atmospheric pressure. The system also allows for the measurement of the amount of fluid transferred from the first side to the second side.

BRIEF DESCRIPTION OF THE DRAWING

Preferred, non-limiting embodiments of the present invention will be described by way of example with reference to the accompanying drawing, in which.

DETAILED DESCRIPTION OF THE INVENTION

Figure 1:
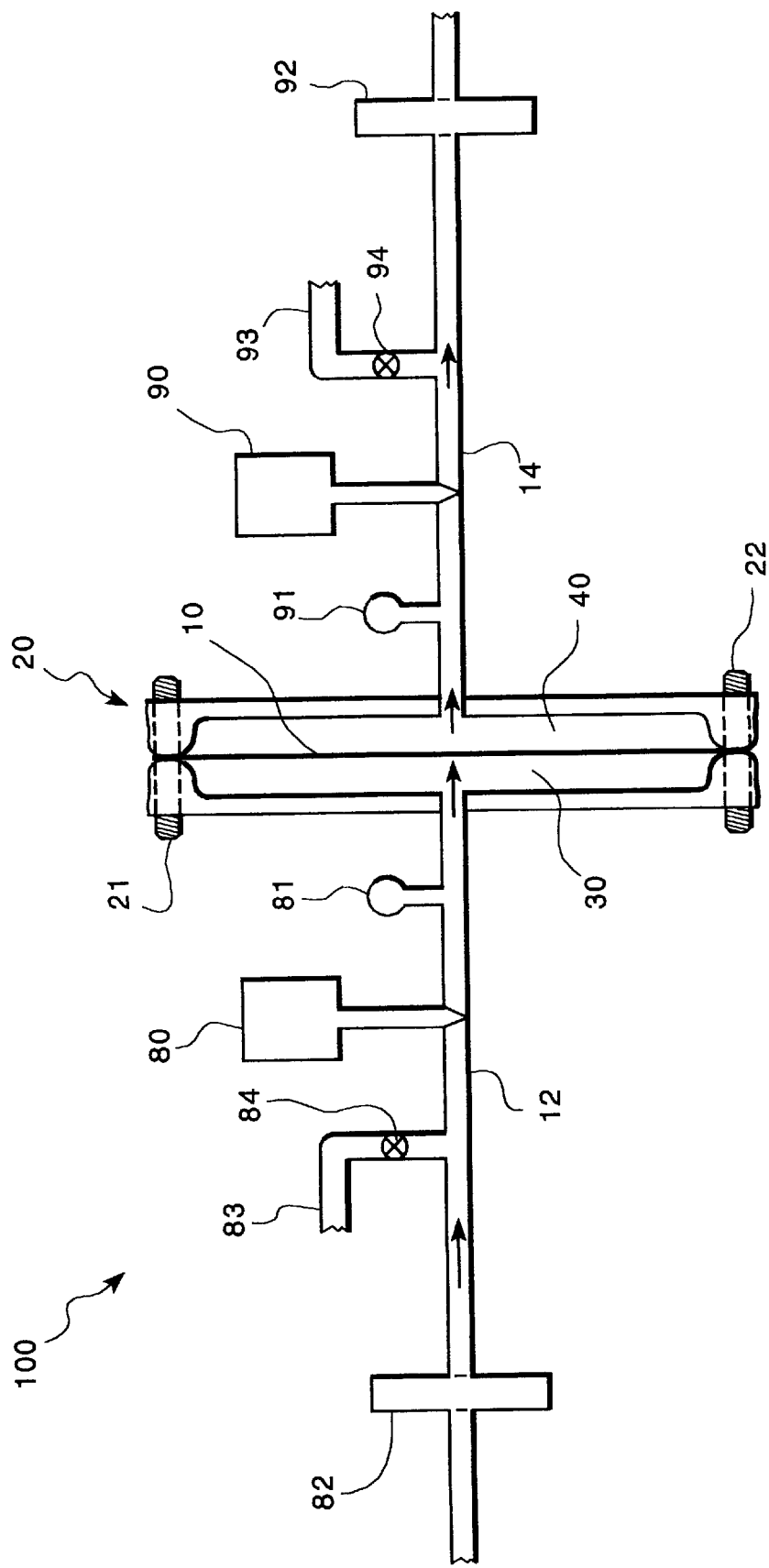
FIG. 1 is a schematic drawing of an embodiment of the apparatus of the invention.

The present invention is directed to a method and apparatus for evaluating the integrity of porous membranes. The method greatly increases the sensitivity of membrane integrity tests and provides the operator with a technique for detecting a single defect, for example, just large enough to allow the passage of a microorganism. The apparatus of the invention provides a system for performing a sensitive membrane integrity test.

Porous membranes are widely used in the treatment of water for a variety of end uses including residential and commercial consumption, industrial processes and pharmaceutical production. Increased demand for high quality water has been driven by increased production of pharmaceuticals and microchips as well as by government regulation. In particular, recent outbreaks of Giardia and Cryptosporidium in drinking water supplies have piqued awareness of these organisms and brought their control to the forefront of water quality issues for municipal water suppliers.

Most microorganisms can be controlled through the use of disinfectants such as chlorine, chloramine or ozone. Some life stages of microorganisms, however, particularly cysts and oocysts, are resistant to these treatments and may be resistant to chlorine at levels that are considered safe for a potable water supply. Fortunately, membrane technology has advanced and is capable of filtering large volumes of water while preventing the passage of these organisms.

As membranes are relied upon to reduce particle and microorganism contamination in critical applications, such as potable water production, the integrity of the membrane must be maintained throughout the production process. Unlike chemical disinfection where effective concentrations of disinfectant can be carefully monitored, a failed membrane may allow passage of pathogenic microorganisms without being detected. As a result, extensive work has been done in the area of membrane integrity testing.

Porous membranes perform by allowing passage of water through pores that extend from one side of the membrane to the other. Ideally, each pore in a membrane is large enough to allow the passage of water while preventing the flow of undesirable organisms and particulate matter. Some membranes have pores small enough to exclude dissolved molecules. The term microfiltration (MF) is generally used to describe membranes capable of excluding particles having a diameter greater than 0.1 micron. Ultrafiltration (UF) refers to membranes capable of excluding particles smaller than 0.1 micron, and hyperfiltration (HF), or reverse osmosis (RO), membranes may be capable of excluding extremely small species such as dissolved ionic compounds. Microporous membranes include those membranes having nominal pore sizes of from about 0.01 micron to about 1 micron, and most typically include membranes having nominal pore sizes of about 0.1 micron to about 0.5 micron.

Under stresses caused by factors such as use, disinfection, backwashing, or age, defects may form in membranes that allow the passage of contaminants that the membrane is designed to exclude. As a result, government regulations, manufacturer recommendations, and typical operation require regular testing be performed on membranes that are being used in critical applications.

Many manufacturers specify a BPT limit for their membranes. BPT parameters and detection methods vary widely but the procedure and theory behind the method are generally consistent from test to test. A membrane is first wetted to fill the pores with a fluid that is compatible with the membrane. Typically, the wetting fluid is water. A second fluid, usually air, is supplied to one side of the membrane and the pressure of this fluid is gradually increased. At first, the capillary and surface tension forces in the pores of the membrane resist the influx of the second fluid and the pressure continues to increase with little or no transport of the fluid through the membrane. As the pressure increases, however, the force acting on the column of fluid in any given pore eventually exceeds the forces that are resisting it and the second fluid flows freely through the pore to the other side of the membrane. Generally, the larger the pore size (at its point of smallest diameter) the sooner the breakthrough will occur due to the force acting on the larger surface area. If the breakthrough is significant, the Bubble Point (BP) can be detected by a number of methods. First, the bubbles themselves may be observed forming on the low pressure side of the membrane or floating up through the liquid that is in contact with the low pressure side of the membrane. Alternatively, the rate of increase of the pressure on the upstream side of the membrane will level off as the flow through the membrane increases. The actual flow of the air through the testing system may also be monitored on either side of the membrane. The formation of bubbles may also be detected acoustically by detecting the difference in sound between the second fluid diffusing through the membrane and the second fluid flowing freely through the pores of the membrane. The increase in flow that occurs at the bubble point may also be measured by using a tracer gas that may be detected by instrumentation on the downstream side of the membrane.

In a DT, a known volume of a gas at a known pressure is in contact with one side of a membrane that has been adequately wetted by a fluid, typically water for a hydrophilic membrane and an alcohol for a hydrophobic membrane. The rate of diffusion through the membrane is measured by monitoring the pressure and/or flow of gas from the high pressure side of the membrane to the low pressure side. This rate of diffusion is then compared to a rate that has been set by the membrane manufacturer for that type of membrane under similar test conditions. If the measured rate surpasses the prescribed rate, a failure may be present in the system.

The BPT and the DT each provide useful information about the membrane being tested and, in tandem, these two tests may provide additional information that is useful to the operator. The transfer model of a fluid by one of these methods, however, is significantly different than the other.

Reliance on the BPT as an accurate measurement of filter integrity assumes that there is a relationship between the bubble point pressure and the size of the potentially largest pore or defect in the membrane. An analytical form of the relationship results from a force balance between wetting and non-wetting fluids in a pore or defect that is assumed to be in the form of a cylindrical capillary. The wetting fluid occupies the pores or defects in the membrane and opposes the force of the non-wetting fluid due to capillary and surface tension forces that are affected by, for example, the wetting fluid itself, the shape of the pores or defect, and the material of which the surface of the membrane is constructed. The Young-LaPlace equation may provide an effective model for equating the BP and the largest pore or defect:

$$\Delta P = 4\sigma(\cos \theta)/d; \quad \text{(Eq. 1)}$$

where $\Delta P$ is the pressure differential across the membrane filter, $\sigma$ is the surface tension of the wetting fluid, $\theta$ is the contact angle between the wetting fluid and the circumference of the capillary, and d is the diameter of the largest pore of the filter.

Although the Young-LaPlace equation may provide a useful predictor of the largest pore or defect, the quantitative predictions of this simplified equation do not match actual bubble point measurements for most microporous filters of a given pore size rating. This likely indicates either a deficiency in the assumptions of the equation, a deficiency in the rating of the pore size, or both. Often, a rating is determined through the use of challenge testing to determine the removal efficiency of particles of known dimensions rather than through actual physical measurement of pore size.

The pores of most microporous membranes, when viewed under a microscope, do not resemble cylindrical capillaries, and if, for example, one were to model a membrane as an array of polymeric columns rather than an array of cylindrical holes, the resulting force balance relationship between pore size and BP would be characterized not only as a function of equivalent pore diameter but also porosity. Porosity, K, is defined as the volume percent of the membrane that is occupied by the space of the pores. For a columnar model, porosity may be defined as K where $$K = 1 - \left[\frac{\pi s^2}{2(d+s)^2}\right] \quad \text{(Eq. 2)}$$

where d is the distance between two diagonally opposed columns in a square array (effective pore size) and s is the column diameter.

The columnar model equates bubble point pressure with column size and porosity.

$$\Delta P = \frac{\pi\sigma(\cos\theta)s}{\left[\Psi^2 - \left(\frac{\pi s^2}{4}\right)\right]} \quad \text{(Eq. 3)}$$

where σ is the surface tension of the wetting fluid, θ is the contact angle, s is the column diameter and Ψ is the closest distance between two columns in a square array. The effective pore size, d, and Ψ can be related based on the Pythagorean Theorem.

Using such a model, the predicted bubble point pressures more closely approximate those typically measured in most microporous filters. For example, using pure, room temperature water as the wetting fluid and assuming air displacement of a completely hydrophilic membrane, an actual pore of diameter 0.28 micrometer and a porosity of 85% would result in a calculated BP of about 150 psid using the Young-LaPlace equation and a much more commonly empirically measured 60 psid if one were to assume an array of equally spaced, equal diameter cylindrical filter media columns with a porosity of 85%. Using a result of a 60 psid BP, the Young-LaPlace equation would predict a largest pore diameter of 0.7 micrometer, whereas a columnar model would predict a largest pore diameter of 0.28 micrometer.

Microporous membranes probably consist of regions that act as capillaries and regions that act as columns and, therefore, the BP probably cannot distinguish between an area of small pores in an isolated region of high porosity and a single large defect many times larger than the rating of the filter. Using either model, however, it may be assumed that there are no pores or defects that are larger than that predicted by the Young-LaPlace equation and, therefore, the implementation of this model may be characterized as avoiding the possibility of false negative results.

However, there may be other limitations of the BPT as an integrity test. From a practical standpoint, and continuing with the example of a 60 psid BP microporous membrane filter, the flow of the non-wetting fluid, typically air, through a single blown-out pore of 0.7 micrometer diameter may not be visible or readily detectable as a free-flowing gas stream, even under laboratory conditions.

If entrance and exit effects are discounted, the compressible molar flow rate, N, of an ideal gas through a cylindrical capillary may be modeled by the Hagen-Poiseuille equation:

$$N = \Pi d^4 g(P_2^2 - P_1^2)/256 \, \mu LRT; \quad \text{(Eq. 4)}$$

where $P_2$ is the absolute inlet pressure and $P_1$ is the absolute outlet pressure across the membrane, d is the pore diameter, g is the gravitational constant, μ is the gas viscosity, L is the length of the pore, R is the gas constant and T is the temperature in degrees Kelvin. For d=0.7 micrometers, $P_2$ of 4 atmospheres absolute, $P_1$ of 1 atmosphere absolute, μ of 0.018 centipoise (typical of air at 298 K.), and L of 250 micrometers (a typical thickness of a microporous membrane,) the molar flow through a single largest pore would be approximately $4\times10^{-11}$ gmole/sec (corresponding to a volumetric flow at 1 atmosphere absolute of about $6\times10^{-5}$ cc/min)—a quantity likely to be too low to be routinely measured in a practical filtration application. Based on direct measurements of the relatively large volume of gas flow at the visible BP, it is likely that a given BP measurement actually detects a relatively large, integral region of low porosity, rather than a non-integral membrane defect.

Although an integrity test based on the BP may be incapable of the requisite sensitivity to detect a single sub-micron sized defect in a porous membrane filter, it is clearly of value in determining whether larger or numerous defects, i.e., detectable defects, exist. In order to approximate the size of a practically measurable defect, it may be helpful to include the contribution provided by diffusion of the non-wetting fluid across the membrane.

The diffusion test and its variant, the pressure hold test, may both provide data as to the amount of non-wetting fluid that is transported through the membrane absent expulsion of wetting fluid from the pores or defects of the membrane. If the diffusion test resulted in zero flow across the membrane, then any flow detected below the rated BP pressure could be attributed to a defect. In practice, however, gasses such as air dissolve in the wetting liquid, diffuse through the pores under the pressure gradient, and desorb on the low pressure side. The relationship between the molar rate of gas transport and the applied pressure differential has been proposed by Reti.

$$N = D(\Delta C)\epsilon/L; \quad \text{(Eq. 5)}$$

where N is the molar permeation rate, D is the diffusivity of gas in the membrane, ε is a porosity/tortuosity factor, ΔC is the molar concentration gradient of gas across the membrane, and L is the thickness of liquid in the membrane (equal to the membrane thickness if the membrane is fully wetted with liquid).

Substitution of Henry's Law ($P_g = HX_g$, where $P_g$ is the gas pressure, H is the Henry's Law constant, and $X_g$ is the mole fraction of gas in the liquid) for the relationship of concentration and applied gas pressure, and assuming that the mole fraction of gas in the liquid is small (as proposed by Emory) yields:

$$N = D(\Delta P)\epsilon \rho_1/LH(MW_1); \quad \text{(Eq. 6)}$$

where (ΔP) is the pressure differential across the membrane, $\rho_1$ is the liquid density, and $(MW_1)$ is the gram-molecular weight of the liquid.

For most microporous filters, at pressure differentials of about 80% of the BP pressure or less, N is typically linear with ΔP. At pressure differentials above about 80% of the BP it is believed that the rate of diffusion may increase due to a shortening of the path of diffusion, L, through the wetting fluid. This may be the result of depression of the meniscus of the wetting fluid (or even partial expulsion of the column of wetting fluid) in the pores as a result of the increased pressure.

Since any non-linearity between N and ΔP, especially below about 80% of the BP pressure, would indicate a loss of membrane integrity, under controlled conditions with predetermined experimental values of ρ and L for a given filter, a diffusion test that measures N as a function of ΔP is capable of higher sensitivity than the bubble point test. However, the condition of a membrane in commercial use changes constantly after being put into service. For example, in applications such as drinking water filtration, membrane fouling may be a common occurrence. In these situations, it is conceivable that ρ, or L, or both, could vary so as to decrease the value of N. In such a case a newly formed membrane defect on a fouled membrane may go undetected because of a decrease in the rate of diffusion across the membrane due to the fouling, i.e., gas transport normally attributed to diffusion would actually be transported through a defect. However, if one neglects any contribution made by diffusion and assumes that all of the transport of fluid across the membrane (below the BP pressure) is a result of flow through a defect and the measured value of N is less than that predicted by the flow through a defect of a specific diameter, then it may be a safe assumption that no defect of the specific diameter, or larger, exists. This may be true even if the fouling of the membrane had built up to such an extent that the contribution to N provided by diffusion is zero. This may also hold true when other factors such as filter construction or time-dependent phenomena serve to cancel part of the contribution that is assumed to be made by the diffusive component (such as may result from a decrease in σ or an increase in θ.)

If one assumes that mass flow N is generated by a defect rather than gaseous diffusion, one can improve the sensitivity of the test by decreasing the diffusive component of N or by increasing the rate of Poiseuille flow relative to diffusive flow for a given defect size in a given membrane. For example, it may be possible to use gas/liquid combinations with D and/or H values lower than air/water. Another possibility can be seen by comparing the equation for laminar flow to the equation for diffusive flow.

N is a strong function of absolute pressure in the Hagen-Poiseuille equation (Eq. 4) because it is a second order function of the absolute pressures, $P_2$ and $P_1$. Alternatively, N is not a strong function of absolute pressure in the diffusion equation (Eq. 6) as it is a first order function of the absolute pressure differential, ΔP, or $P_2-P_1$. Therefore, performing an integrity test at high pressure differentials (but at a differential lower than the BP,) and under elevated absolute pressure on the downstream side of the filter (rather than at atmospheric pressure) may result in improved test sensitivity. Single defects as small as 10, 5, or even 1 micron in diameter may be detected.

This improvement in test sensitivity may allow for the detection of a single defect of sufficient size to allow passage of a microorganism of concern. It may also allow for more accurate testing of larger membranes and may allow for the testing of multiple membranes in parallel while still being able to detect a single defect of a minimum size.

FIG. 1 illustrates one embodiment of the apparatus of the invention that may be used to practice a method of the invention. The apparatus 100 may be a system that is designed specifically for testing the integrity of a membrane, for example, in a laboratory, or it may be a working filtration system of a municipal water supply or other filter system where the filter is tested in situ. FIG. 1 illustrates an apparatus that is designed specifically for testing membranes.

The apparatus includes a membrane 10 that may be any type of porous membrane. The membrane that is being tested may be designed to remove either particles or dissolved species from a fluid and includes those filters designed for MF and UF. The membrane may be of any size or shape and may be, for example, in the form of a flat disk or sheet, a fluted sheet, a cylindrical cartridge, a fiber, a capillary, or a wound filter. The membranes are generally less than 500 microns in thickness and are usually between about 100 and 300 microns thick. Multiple membranes may be tested concurrently, as total membrane area is more important than the number of membranes being tested in parallel. The membrane may be hydrophilic or hydrophobic and may be comprised of more than one type of material. For example, the membrane may have a coating to improve its filtering characteristics. Some examples of polymers that may be used in the membranes are sulfone polymers, for example, polyethersulfone; fluorinated polymers, for example, PVDF and PTFE; polyolefins, for example, polypropylene; and cellulosics, for example, cellulose esters.

FIG. 1 shows a disk shaped membrane 10. The membrane 10 is held in a pressure resistant housing 20 that may be the same housing that is used to hold the membrane during normal operational filtration. The membrane divides the pressure resistant housing into two separate chambers, 30 and 40. Chambers 30 and 40 are isolated from each other by the membrane. Chambers 30 and 40 of the housing, are held together, for example, by bolts 21, 22, which may also serve to secure membrane 10 in place.

Membrane 10 is wetted with a wetting fluid. Preferably, the wetting fluid is chosen so that it does not adversely affect the membrane or the end product of the process. If the membrane is hydrophilic, water is the preferred wetting fluid; if the membrane is hydrophobic, an alcohol, preferably methanol or isopropanol, may be used as the wetting fluid. The membrane is thoroughly wetted with the fluid, preferably so that the pores of the membrane are filled with fluid while the air in the pores has been expelled. The wetting may be accomplished by allowing the membrane to float in the wetting fluid for an adequate length of time to expel the air from the pores.

In operation, to start the testing procedure, chambers 30, 40 may be pressurized above atmospheric pressure. Chamber 40, the downstream chamber, may be pressurized with any fluid. Preferably, the chamber is pressurized with a fluid that is at least partially immiscible in the wetting fluid. A partially immiscible fluid is a fluid that is soluble in the wetting fluid at a level below about 1 g/100 g, for example, carbon dioxide in water. Pressure may be provided by a pump or other source of compressed fluid, that is in communication with conduit 14. An effective pressure is defined as a pressure on the downstream side of the membrane at which the Poiseuille flow is at least about 50% greater than is the Poiseuille flow at an equivalent pressure differential with the downstream side of the membrane at atmospheric pressure. A pressure sensing device 91 is in communication with the chamber 40 and may be placed along the test line where it is capable of reading the pressure in chamber 40. Preferably, the pressure sensing device 91 is a barometric device capable of measuring pressure accurately up to a pressure above 10 atmospheres. Most preferably, device 91 is a pressure transducer that may provide data to a computer that may then be used to facilitate the operation of the present testing procedure.

Chamber 30 is pressurized with a fluid that is at least partially immiscible with the wetting fluid. Preferably, the pressurizing fluid is substantially immiscible in the wetting fluid. A substantially immiscible fluid has a solubility in the wetting fluid lower than that of carbon dioxide in water, for example, the solubility of air or nitrogen in water. The fluid should not damage the membrane and preferably is not deleterious to the product that is being filtered. Most preferably, the fluid is chosen in combination with the wetting fluid so that it exhibits low diffusivity, D and a low Henry's Law constant, H. If water is used as the wetting fluid, air or nitrogen is preferred as the pressurizing fluid.

The pressurizing fluid may be provided by a pump, by a tank of pressurized fluid, or by any other source capable of achieving the pressures required to operate the test procedure. In FIG. 1, the pressurized fluid is supplied through conduit 12. In this example, the flow and pressure of air is controlled by regulator 82. Pressure sensor 81 monitors the pressure on the upstream side of the membrane. Pressure sensor 81 may be similar to pressure sensor 91, and preferably is a pressure transducer that is in communication with a computer to control the operation of the present procedure or to record pressure data.

The pressure on both sides of the membrane, in chambers 30, 40, may be brought up to pressure concurrently. For example, as low pressure fluid is fed to chamber 40 by regulator 92, the high pressure fluid is fed into pressurized chamber 30. While both sides of the system are being pressurized, it is preferred that any pressure differential between the two sides be kept below the bubble point pressure. Most preferably, the pressure differential is kept below about 80% of the bubble point pressure. Once chamber 40, the downstream chamber, has reached the desired test pressure, flow to the chamber ceases. The pressure may be monitored to assure that there are no leaks on the downstream side of the system. The high pressure fluid, being supplied to chamber 30, continues to flow into chamber 30 until a desirable upstream pressure is attained. Regulators 82 and 92 may serve to keep the pressure on each side of the membrane constant throughout the procedure.

The desired upstream testing pressure may be determined in a number of ways. For example, if an operator is concerned about defects of a certain diameter, X, the absolute pressures in chambers 30, 40 should preferably be set so that the anticipated rate of diffusion through the membrane is less than that which would be predicted by the flow through a single defect of size X. For example, if the diffusional flow through a specific membrane was calculated or determined to be 10 cc/min at a pressure differential of 50 psi, then the absolute pressures in chambers 30, 40 may be raised to a pressure whereby at the same differential, 50 psi, the difference of the squares of the two absolute pressures is great enough to result in a flow through a single defect of size X that is greater than 10 cc per minute. The absolute pressures that can be obtained may be controlled by other factors such as the pressure holding capabilities of the filter housing and the pressures obtainable by the pumps or other pressure sources supplying fluid to both sides of the membrane. It is most preferable to operate the test at a pressure differential of at least about 50% of the bubble point pressure, as a greater pressure differential between the two sides of the membrane will magnify the amount of flow that is provided by flow through a defect (the Hagen-Poiseuille equation) when compared to the amount provided by diffusion through the membrane.

Once the target pressures are achieved on both sides of the membrane, the flow across the membrane may be measured, for example, by measuring changes in volume, mass flow, or pressure. For example, the flow may be monitored by a flow measuring device 80 or 90, positioned so that it can measure either the flow of fluid into chamber 30 or the flow of fluid out of chamber 40. Any device capable of measuring the flow of fluid may be used. Preferably, a mass flow meter is used because it is capable of accurately measuring mass flow regardless of the pressure of the fluid. It is most preferable that the fluid being measured is first dried so that results are not biased by the presence of water in the fluid. A mass flow detector may be positioned upstream of the membrane, downstream of the membrane, or in both positions.

Once an accurate flow has been measured from chamber 30 to chamber 40, the results may be compared to a standard that may be provided by the membrane manufacturer or supplier or, alternatively, may have been determined empirically on the same or a similar membrane. The standard may be based on a typical diffusion rate, the rate of flow attributable to a defect of a specific size, or any other number of different standards. If the measured flow rate exceeds the standard, then the membrane being tested may be considered to have failed the test, and the operator may proceed appropriately. If the flow rate is below the standard level for that membrane, the membrane may be put back on line and into productive use because no defects greater than the size measured are contained in the membrane. This may be true regardless of any fouling that may be present on the membrane or any other change to the membrane or the filter system.

Once the test is complete, pressure may be released through vents 83, 93 by opening valves 84, 94, respectively.

EXAMPLE 1

In order to evaluate the effectiveness of the present testing procedure, a diffusion test was run on a membrane of known characteristics at elevated absolute pressures. The results were then compared to the flow that would be calculated from the Hagen-Poiseuille equation for a defect of a size adequate to allow passage of a single Cryptosporidium oocyst through the same membrane.

A microporous filter cartridge (Millipore 0.22 micrometer rating, catalog #FCPV01032, available from Millipore Corporation, Bedford, Mass.) was tested for diffusion rate at different pressure differentials and absolute pressures. At a 15 psi pressure differential, the volumetric diffusion rate (at atmospheric pressure and room temperature) was measured to be an average of 3.9 cc/min at a 30 psia downstream pressure; 3.8 cc/min at a 45 psia downstream pressure; and 3.2 cc/min at a 60 psia downstream pressure. At a 30 psi pressure differential, the volumetric diffusion rate was measured to be an average of 6.6 cc/min at a 15 psia downstream pressure; 6.6 cc/min at a 30 psia downstream pressure; and 6.3 cc/min at a 45 psia downstream pressure. The diffusion rate through the filter was approximately proportional to pressure differential and approximately independent of absolute pressure.

Using the Hagen-Poiseuille equation, the estimated air flow was calculated to be 2.2 cc/min for a single 10 micrometer diameter hole under the following conditions: pressure differential of 2 atmospheres, absolute downstream pressure of 1 atmosphere, and membrane thickness of 150 micrometers. A significantly higher rate of flow of 7.7 cc/min was calculated for the same 10 micrometer diameter hole under the following conditions: pressure differential of 2 atmospheres, absolute downstream pressure of 6 atmospheres, and membrane thickness of 150 micrometers.

These results illustrate that by raising the pressure on the downstream side of the membrane to greater than atmospheric pressure, the flow through a defect of a specific size may be increased without an accompanying increase in the diffusive contribution to the flow through the membrane. This shows, for example, that a filter exhibiting a gas flow rate of 6.6 cc/min during a diffusion rate integrity test at a downstream pressure of 6 atmospheres and a pressure differential of 2 atmospheres should not contain a single defect of size 10 micrometers or larger, even assuming that the actual diffusion flow through the membrane was zero and not all the pores were fully wetted.

Further modifications and equivalents of the invention herein disclosed will occur to persons skilled in the art using no more than routine experimentation, and all such modifications and equivalents are believed to be within the spirit and scope of the invention as defined by the following claims.

What is claimed is:

1. A method for evaluating a membrane comprising the steps of:

supplying an at least partially immiscible fluid to a first side of a wetted membrane at a first pressure greater than a second pressure on a second side of the membrane;

maintaining the second pressure at a constant level;

forming a pressure differential across the membrane, wherein an amount of Poiseuille flow through the membrane is at least about 50% greater than an amount of Poiseuille flow that would occur through the membrane at the same pressure differential and when the second side of the membrane is at atmospheric pressure; and measuring a rate of transfer of the fluid from the first side of the membrane to the second side of the membrane.

2. The method of claim 1 further comprising the step of comparing the rate of transfer of the fluid to a second rate of transfer.

3. The method of claim 2 wherein the second rate of transfer is a predicted rate of diffusion of the fluid through the membrane.

4. The method of claim 2 wherein the second rate of transfer is the rate predicted by a rate of transfer of the fluid through a defect of a specific size.

5. The method of claim 4 wherein the specific size defect is of a size adequate to allow passage of a microorganism.

6. The method of claim 5 wherein the microorganism is a Cryptosporidium oocyst.

7. The method of claim 5 wherein the microorganism is a Giardia cyst.

8. The method of claim 4 wherein the specific size defect has a diameter of less than about 10 microns.

9. The method of claim 8 wherein the specific size defect has a diameter of less than about 5 microns.

10. The method of claim 9 wherein the specific size defect has a diameter of less than about 1 micron.

11. The method of claim 1 wherein the fluid is substantially immiscible with a fluid used to wet the membrane.

12. The method of claim 11 wherein the substantially immiscible fluid is air.

13. The method of claim 1 wherein the pressure differential is less than about 80% of a bubble point pressure of the membrane.

14. The method of claim 1 wherein the pressure differential is more than about 15 psi.

15. The method of claim 14 wherein the pressure differential is more than about 30 psi.

16. The method of claim 15 wherein the pressure differential is more than about 60 psi.

17. The method of claim 1 wherein the absolute pressure on the second side of the membrane is greater than about 2 atmospheres.

18. The method of claim 17 wherein the absolute pressure on the second side of the membrane is greater than about 4 atmospheres.

19. The method of claim 18 wherein the absolute pressure on the second side of the membrane is greater than about 10 atmospheres.

20. The method of claim 1 further comprising the step of providing water to the second side of the membrane.

21. The method of claim 1 wherein the membrane comprises a capillary.

22. The method of claim 1 wherein the membrane comprises a fiber.

23. The method of claim 1 wherein the rate of transfer is measured downstream of the membrane.

24. The method of claim 1 further comprising the step of providing a liquid to the second side of the membrane.

25. A method for detecting a defect in a membrane comprising the steps of:

pressurizing a first side of the membrane to a pressure greater than a pressure on a second side of the membrane to produce a pressure differential, wherein an amount of Poiseuille flow through the membrane is at least about 50% greater than an amount of Poiseuille flow that would occur through the membrane at the same pressure differential when the pressure on the second side of the membrane is at atmospheric pressure;

maintaining the pressure on the second side of the membrane at a constant pressure;

measuring the amount of fluid transferred from the first side of the membrane to the second side of the membrane; and comparing the amount of fluid transferred to another amount that is predicted by calculating the expected amount of fluid transfer through a defect of a specific size.

\* \* \* \* \*